United States Patent [19]

Meilland

[11] Patent Number: Plant 6,177

[45] Date of Patent: May 17, 1988

[54] ROSE PLANT—MEIJETTE VARIETY

[75] Inventor: Marie-Louise Meilland, Antibes, France

[73] Assignee: The Conard-Pyle Company, West Grove, Pa.

[21] Appl. No.: 838,661

[22] Filed: Mar. 11, 1986

[51] Int. Cl.[4] ..... A01H 5/00

[52] U.S. Cl. ..... Plt./8

[58] Field of Search ..... Plt. 8

*Primary Examiner*—Robert E. Bagwill

*Attorney, Agent, or Firm*—Burns, Doane, Swecker & Mathis

[57] ABSTRACT

A new and distinct variety of rose plant of the Miniature Class is provided which forms in abundance attractive yellow double blossoms. The blossoms are minosa yellow in coloration and are of a relatively long duration while present on the plant. The plant exhibits a vigorous growth habit which forms compact and regular vegetation.

1 Drawing Sheet

SUMMARY OF THE INVENTION

The new variety of Miniature rose plant was created by artificial pollination wherein two parents were crossed which previously had been studied in the hope that they would contribute the desired characteristics. The female parent (i.e., the seed parent) of the new variety was formed by crossing the Rumba variety (U.S. Plant Pat. No. 1,919) with the variety Carol Jean (U.S. Plant Pat. No. 4,277). The male parent (i.e., the pollen parent) of the new variety was formed by crossing the Meialfi variety with variety Meilucca. The parentage of the new variety can be summarized as follows:

(Rumba × Carol Jean) × (Meialfi × Meilucca).

The seeds resulting from the above pollination were sown in a greenhouse and 56 plantlets were obtained which were physically and biologically different from each other. Selective study resulted in the identification of a single plant of the new variety.

It was found that the new variety of Miniature rose plant of the present invention possesses the following combination of characteristics:

(a) forms in abundance attractive double blossoms which are mimosa yellow in coloration and of long duration on the plant, and
(b) exhibits a vigorous growth habit which results in the formation of compact and regular vegetation.

The new variety well meets the needs of the greenhouse floricultural industry and horticultural industry for many usages. For instance, the new variety can be grown as attractive ornamentation in parks and gardens. The resulting plant is very strong and vigorous.

The new variety has been found to undergo asexual propagation by a number of routes, including budding, winter bench grafting, etc. The characteristics of the new variety have been found to be strictly transmissible by such asexual propagation from one generation to another.

The new variety has been named the Meijette variety.

BRIEF DESCRIPTION OF THE PHOTOGRAPH

The accompanying photograph shows as nearly true as it is reasonably possible to make the same, in a color illustration of this character, typical specimens of the plant parts of the new variety. The rose plants of the new variety described herein were one year old and observed during December while growing on their own roots in a greenhouse at Cannet de Maures, Var, France.

DETAILED DESCRIPTION

Figures 1, 2, 3, 4, 5, 6, 7, 8, 9, 10, 11, 12, 13, 14, 15, 16:
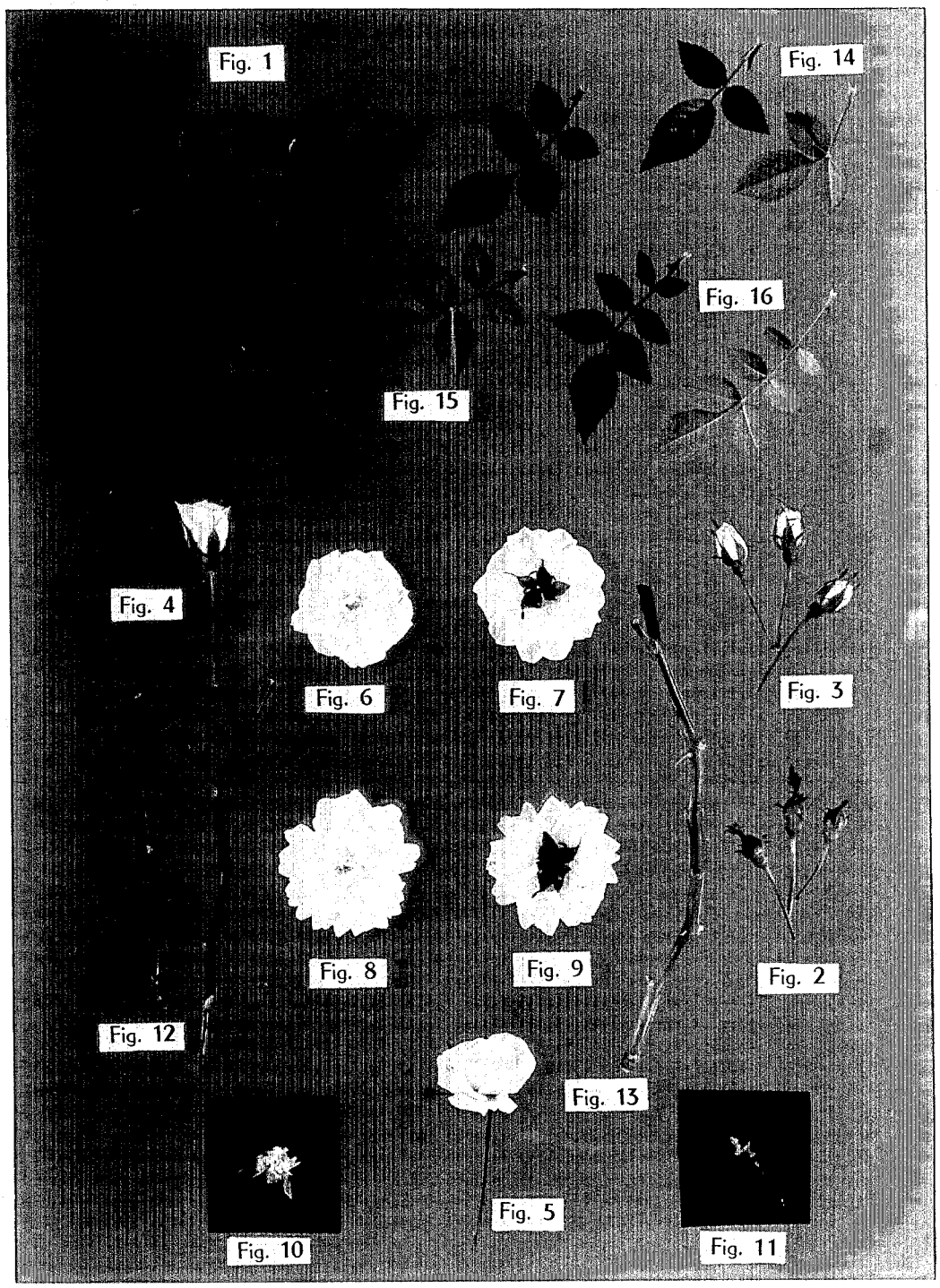
FIG. 1 illustrates a specimen of a young shoot.
FIG. 2 illustrates a specimen of a cluster of floral buds before the opening of the sepals.
FIG. 3 illustrates a specimen of a cluster of floral buds before the opening of the sepals.
FIG. 4 illustrates a specimen of a floral bud at the opening of the petals.
FIG. 5 illustrates a specimen of a flower in the course of opening.
FIG. 6 illustrates a specimen of a fully open flower - plan view - obverse.
FIG. 7 illustrates a specimen of a fully open flower - plan view - reverse.
FIG. 8 illustrates a specimen of a fully open flower immediately prior to petal drop - plan view - obverse.
FIG. 9 illustrates a specimen of a fully open flower immediately prior to petal drop - plan view - reverse.
FIG. 10 illustrates a specimen of a floral receptacle showing the arrangement of the stamens and pistils.
FIG. 11 illustrates a specimen of a floral receptacle showing the arrangement of the pistils (stamens removed)
FIG. 12 illustrates specimens of flowering stems.
FIG. 13 illustrates a specimen of a main branch.
FIG. 14 illustrates specimens of leaves with three leaflets with the upper surface being shown on the left and the under surface being shown on the right.
FIG. 15 illustrates specimens of leaves with five leaflets with the upper surface being shown on the top and the under surface being shown on the bottom.
FIG. 16 illustrates specimens of leaves with seven leaflets, with the upper surface being shown on the left and the under surface being shown on the right.

The chart used in the identification of the colors is that of The Royal Horticultural Society (R.H.S. Colour Chart). The description is based on one year old specimens of the new variety during December while growing in a greenhouse on their own roots at Cannet de Maures, France.

Class: Miniature.

Plant:

*Height.*—approximately 20 to 25 cm.

*Habit.*—Bushy.

Branches:

Color.—Young stems: Yellow-Green Group 144A somewhat suffused with reddish brown. Adult wood: light green, Yellow-Green Group 137C.

Leaves:

*Petioles.*—Upper surface: light green on young foliage, medium green on adult foliage with more or less glandular margins. Under surface: light green with relatively long thorns.

*Leaflets.*—Number: 3, 5, and 7 (most often). Shape: lancelate. Serration: simple and regular. General appearance: ample, dense, and glossy. Color (young foliage): upper surface: Yellow-Green Group 144A. under surface: Yellow-Green Group 144B. Color (adult foliage): upper surface: medium green, Yellow-Green Group 137A. under surface: Yellow-Green Group 137C.

Inflorescence:

*Number of flowers.*—Usually one per stem.

*Peduncle.*—Its length is approximately 3.5 cm. on average, light green in coloration often with reddish-brown spots.

*Buds.*—Shape: substantially round. Length: approximately 0.7 cm. on average. Color upon opening: upper surface: canary yellow, Yellow Group 9A. under surface: canary yellow, Yellow Group 9A.

Flower.—Shape: slightly flat. Diameter: approximately 2.5 cm. on average. Color (when opening begins): upper surface: mimosa yellow, Yellow Group 8A, with deeper yellow towards center. under surface: mimosa yellow, Yellow Group 8A, with deeper yellow towards center. Color (when partially open): upper surface: light mimosa yellow, Yellow Group 8B towards the center, Yellow Group 8C towards the outside. under surface: creamy yellow, Yellow Group 8D. Color (at end of opening): upper surface: light creamy yellow, Yellow Group 8D, with whitening. under surface: light creamy yellow, Yellow Group 8D, with whitening. Fragrance: none. Lasting quality: long on plant. Petal number: approximately 90 to 95 on average. Petal form: external: flat with curled margins. internal: oval at the beginning and pointed on the tip. Stamen number: approximately 12 on average, sometimes none. Anthers: yellowish.

I claim:

1. A new and distinct variety of Miniature rose plant characterized by the following combination of characteristics:

(a) forms in abundance attractive double blossoms which are mimosa yellow in coloration and of long duration on the plant, and (b) exhibits a vigorous growth habit which results in the formation of compact and regular vegetation;

substantially as herein shown and described.

* * * * *